United States Patent [19]

Brüngger et al.

[11] Patent Number: 5,648,550
[45] Date of Patent: Jul. 15, 1997

[54] BETA-KETO-ALCOHOLS AND THE PROCESS FOR THE MANUFACTURE THEREOF

[75] Inventors: Andreas Brüngger, Volketswil; Hansjörg Gründler, Rheinfelden; Werner Simon, Riehen, all of Switzerland

[73] Assignee: Roche Vitamins Inc., Paramus, N.J.

[21] Appl. No.: 567,818

[22] Filed: Dec. 6, 1995

[30] Foreign Application Priority Data

Dec. 8, 1994 [CH] Switzerland ............... 3713/94
Oct. 18, 1995 [CH] Switzerland ............... 2952/95

[51] Int. Cl.⁶ ............................................. C07C 45/45
[52] U.S. Cl. ................................. 568/388; 585/351
[58] Field of Search ....................... 568/388; 585/351

[56] References Cited

FOREIGN PATENT DOCUMENTS 630 578   12/1994   European Pat. Off. .
0630578   12/1994   European Pat. Off. .

OTHER PUBLICATIONS

Aguilar–Martinez, M., et al., *ACTA Chem. Scand.*, 26(6):2528–30 (1972).
Arpin, N., et al, *Bull. Soc. Chim. Biol.*, 49(5):527–536 (1967).
Arpin, N., et al., *Chemical Abstracts*, 67(21):9202 Abstract No. 097953 (1967).
Inoue, et al. Chemistry Letter, pp. 1377–1378 (1991).
Aguilar–Martinez et al; ACTA Chem. Scand.; 26(6):2528–2530 1972.
Inoue et al; Chemistry Letters; pp. 1377–1378 1991.

*Primary Examiner*—C. Warren Ivy
*Assistant Examiner*—Sreeni Padmanabhan
*Attorney, Agent, or Firm*—George W. Johnston; William H. Epstein; Lewis J. Kreisler

[57] ABSTRACT

A novel process for the manufacture of β-keto alcohols from aldehydes comprising reacting a conjugated polyene aldehyde under basic conditions with a cyclocarbonate or derivative thereof. Certain carotenoid products of this process are novel compounds and are also an object of the present invention. The products, which for the most part belong to the carotenoid field, find corresponding use, for example, as colorants or pigments for foodstuffs, egg yolk, integuments and/or subcutaneous fat of poultry and flesh and/or integuments of fish and crustaceans.

11 Claims, No Drawings

BETA-KETO-ALCOHOLS AND THE PROCESS FOR THE MANUFACTURE THEREOF

SUMMARY

The present invention is concerned with a novel process for the manufacture of β-keto-alcohols from aldehydes by a special condensation reaction, as well as certain novel products of this process.

The novel process of the invention comprises reacting an optionally substituted conjugated polyene aldehyde with a cyclic α-methylene carbonate under basic conditions to produce β-keto alcohols. The formyl group terminally bonded to the conjugated double bond of the polyene aldehyde is converted into a group —CH=CH—CO—CR$^1$R$^2$OH, wherein R$^1$ is an alkyl group and R$^2$ is an alkyl or alkenyl group, or R$^1$ and R$^2$ together are 1,4-tetramethylene or 1,5-pentamethylene.

DETAILED DESCRIPTION OF THE INVENTION

Chemistry Letters 1991, 1377–1378 (Inoue et al.) discloses a cycloaddition reaction between a cyclic α-methylenecarbonate, namely 4,4-dimethyl-5-methylene-1,3-dioxolan-2-one (hereinafter "cyclocarbonate"), and an aromatic aldehyde with the cleavage of carbon dioxide to give a 2,2-dimethyl-5-aryldihydrofuran-3-one. This reaction is carried out using a variety of catalysts containing palladium or another transition metal. When benzaldehyde is used as the aromatic aldehyde, the reaction also proceeds in the presence of a Lewis acid, e.g. zinc chloride or aluminium chloride, as the catalyst, whereby however 2-methyl-3-oxo-5-phenylpent-4-en-2-ol [C$_6$H$_5$CH=CHCOC(CH$_3$)$_2$OH] and/or another byproduct is also obtained. Neither the use of a base instead of the catalyst containing a transition metal nor the use of aldehydes other than aromatic aldehydes (ArCHO) is reported in this literature reference.

It has now surprisingly been found that the aforementioned cyclocarbonate reagent or a derivative thereof is very well suited for the conversion of a formyl group —CHO situated at the terminal position of the conjugated chain of an optionally substituted conjugated polyene aldehyde into a 4-hydroxy-4-methyl-3-oxo-1-pentenyl group —CH=CH—CO—C(CH$_3$)$_2$OH or a corresponding derivative when the reaction of the aldehyde with the cyclocarbonate or derivative thereof is carried out under basic conditions. The term "optionally substituted conjugated polyene aldehyde" embraces not only respective monoaldehydes (A—CHO) but also respective dialdehydes (OHC—B—CHO), whereby in is the latter case both free terminal formyl groups are converted into the 4-hydroxy-4-methyl-3-oxo-1-pentenyl group or a corresponding derivative. Accordingly, the present invention comprises a process for the conversion of an optionally substituted conjugated polyene aldehyde of the general formula

A—CHO      I' or

OHC—B—CHO      I"

wherein

A is a monovalent optionally substituted conjugated polyene chain connected at the terminal position of this chain, and B is a divalent optionally substituted conjugated polyene chain connected at the terminal positions of this chain, into a polyene (di)alcohol of the general formula

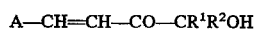
A—CH=CH—CO—CR$^1$R$^2$OH      II' or, respectively,

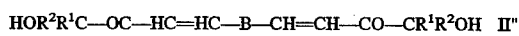
HOR$^2$R$^1$C—OC—HC=HC—B—CH=CH—CO—CR$^1$R$^2$OH      II"

wherein

R$^1$ is a C$_{1-6}$-alkyl group and

R$^2$ is a C$_{1-6}$-alkyl group or a C$_{2-6}$-alkenyl group or

R$^1$ and R$^2$ together form 1,4-tetramethylene or 1,5-pentamethylene, which process comprises reacting the polyene aldehyde under basic conditions with cyclocarbonate or a derivative thereof of the general formula

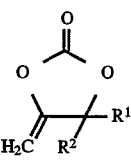

III wherein R$^1$ and R$^2$ have the significances given above. In this manner the (each) formyl group bonded to the terminal conjugated double bond(s) of the optionally substituted conjugated polyene aldehyde is converted into a —CH=CH—CO—CR$^1$R$^2$OH group.

As can be seen from the above, A or B can be derived from an optionally substituted conjugated polyene monoaldehyde or dialdehyde, respectively, which is devoid of the formyl group or of the two formyl groups, respectively, with the formyl group(s) being situated at the terminal position(s) of the conjugated chain of this polyene aldehyde.

The process in accordance with the invention can be used with any substituted or unsubstituted conjugated polyene aldehyde of formula I' or I". The polyene aldehydes used in accordance with this invention are the aforementioned polyene aldehydes A—CHO or OHC—B—CHO which have the —C=C—CHO grouping, e.g. —CH=CH—CHO, —C(CH$_3$)=CH—CHO or —CH=C(CH$_3$)—CHO, at the end or, respectively, at both ends. Included among such polyene aldehydes (educts) are, inter alia, the following subclasses [in which the abbreviated manner of representation (using simple lines) for the structural formulae usual in carotenoid chemistry is used]:

1) Alicyclic-aliphatic polyene aldehydes, which mainly belong to the carotenoid field [as asymmetric carotenoid aldehydes having a six-membered (cyclohexene) ring], of the general formula

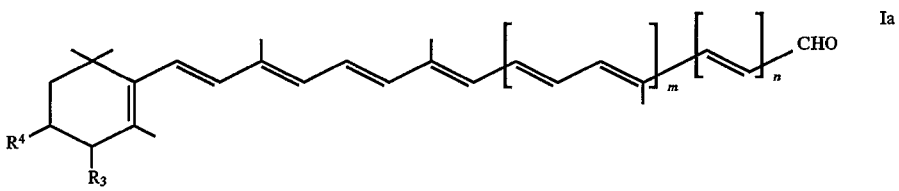

wherein
- $R^3$ and $R^4$ each independently is hydrogen, an optionally protected hydroxy group or an optionally protected oxo group,
- m is 0, 1, 2, 3 or 4 and
- n is 0 or 1, which, after reaction with the compound of formula III under basic conditions, are converted into the corresponding alicyclic-aliphatic polyene alcohols of the general formula wherein
- r is 0, 1 or 2 and
- n is 0 or 1, and in which one of the two formyl groups is optionally protected, which, after reaction with the compound of formula III under basic conditions, are converted into the corresponding aliphatic polyene dialcohols or, respectively, polyene alcohols of the general formula

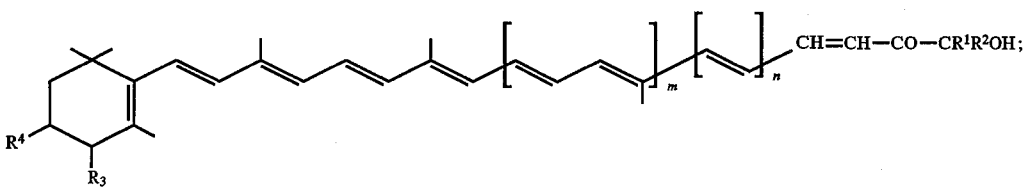

2) aliphatic polyene aldehydes, which also mainly belong to the carotenoid field (as open-chain asymmetric carotenoid aldehydes), of the general formula

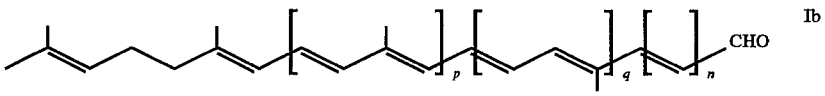

wherein
- p is 0, 1 or 2,
- q is 0, 1, 2 or 3 and
- n is 0 or 1, which, after reaction with the compound of formula III under basic conditions, are converted into the corresponding aliphatic polyene alcohols of the general formula

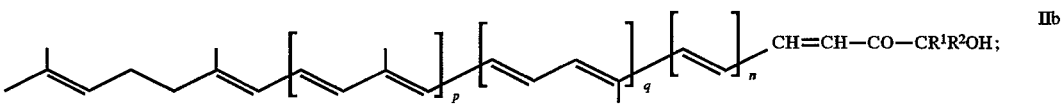

3) aliphatic polyene aldehydes, which also mainly belong to the carotenoid field (as symmetric carotenoid dialdehydes), of the general formula

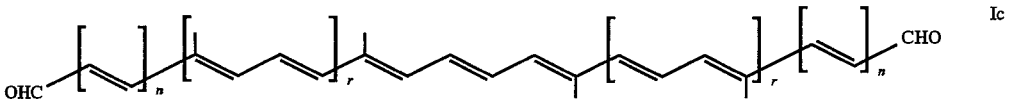

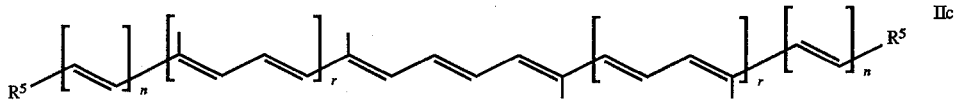

wherein n and r have the significances given above and the two R⁵'s each are the —CH=CH—CO—CR¹R²OH group or one R⁵ is this group and the other is a protected formyl group.

The educts of general formulae Ia, Ib and Ic can be embraced by general formula I:

R—CHO    I wherein

R is a group (a), (b) or (c)

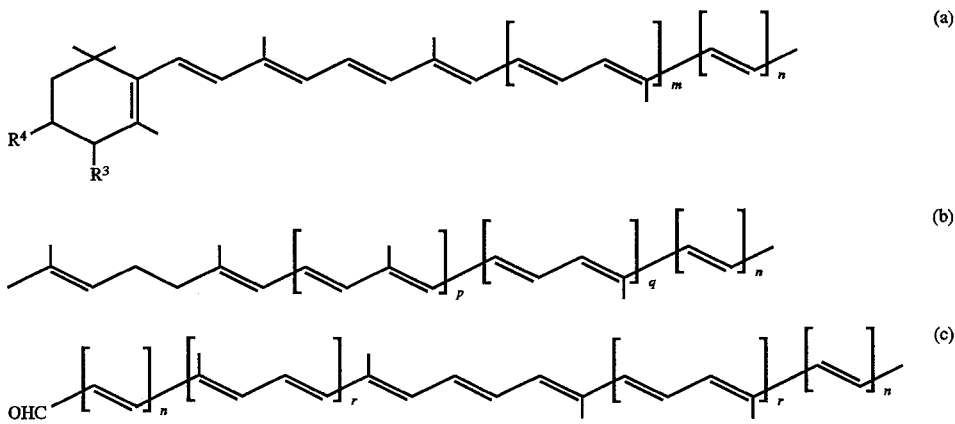

and

R³, R⁴, m, n, p, q and r have the significances given above, with one of the two formyl groups being optionally protected when R is group (c).

After reaction with cyclocarbonate or a derivative thereof of formula III under basic conditions the educt of formula I is converted into the corresponding product of formula II:

R'—CH=CH—CO—CR¹R²OH    II wherein R' has the significance of R given above, with the formyl group being either protected or replaced by the HOR²R¹C—CO—CH=CH— group when R' is group (c).

Where the product of formula II, especially of formula IIa or IIc, contains one or more protecting groups, the protecting group(s) present can be cleaved off if desired, which represents a further aspect of the present invention. For example, in the case of a product of formula II wherein R' is group (c) and the formyl group therein is protected, the formyl protecting group can be cleaved off if desired by conventional means to afford an unprotected formyl group.

In the scope of the present invention the term "$C_{1-6}$-alkyl group" or "$C_{2-6}$-alkenyl group" embraces straight-chain and branched groups such as, for example, methyl, ethyl and isobutyl or, respectively, vinyl and 4-methyl-3-pentenyl. Where R¹ and R² together form 1,4-tetramethylene or 1,5-pentamethylene, the respective grouping —CR¹ R²— (in formulae II, II", III, IIa, IIb and IIc) is cyclopentylidene or, respectively, cyclohexylidene.

As used throughout, the terms "optionally substituted" or "optionally protected" with regards to compounds or groups means that the compounds or groups may be substituted or unsubstituted, or protected or unprotected, respectively.

The term "protected hydroxy group" embraces usual protected hydroxy groups (especially those which are familiar from the carotenoid field), particularly etherified hydroxy groups and acyloxy groups. The "etherified hydroxy groups" are, for example, $C_{1-5}$-alkoxy groups, preferably methoxy and ethoxy; $C_{2-16}$-alkoxyalkyl groups, preferably 1-methoxy-1-methylethoxy; arylalkoxy groups, preferably benzyloxy; tetrahydropyranyloxy; and tri($C_{1-5}$-alkyl) silyloxy groups, preferably trimethylsilyloxy. The acyloxy groups embrace especially alkanoyloxy and aroyloxy groups with preferably up to 8 carbon atoms such as, for example, formyloxy, acetoxy, propionyloxy and benzoyloxy.

The term "protected oxo group" also embraces usual protected oxo groups (especially those which are familiar from the carotenoid field). Acetalized oxo groups, especially those in which the term protected oxo stands for two $C_{1-5}$-alkoxy groups (e.g. for two methoxy groups) or for a $C_{2-6}$-alkylenedioxy group (e.g. ethylenedioxy or 2,3-butylenedioxy), are preferred. Further, an oxo group can also be protected as an enol ether, primarily in the case of α-hydroxyketones (e.g. R³ and R⁴ signify hydroxy and, respectively, oxo or vice versa), whereby the etherification of the enediol can preferably also be effected by the formation of a cyclic acetal or ketal (e.g. with acetone to the acetonide). The oxo group can also be protected, for example, as an imine.

Where an aliphatic polyene aldehyde of formula Ic in which one formyl group is protected is used as the educt, this protected formyl group is conveniently an acetalized formyl group. This is a usual acetalized aldehyde group, especially a di($C_{1-5}$-alkoxy)methyl group, e.g. dimethoxymethyl, or 3-dioxolan-2-yl or an analogous condensate of the formyl group with a $C_{2-6}$-alkylenediol, e.g. 2,2-dimethyltrimethyleneglycol.

Unless further qualified, the term "alkyl" embraces straight-chain and branched groups, preferably with 1–5 carbon atoms, such as, for example, methyl, ethyl, n-propyl, isopropyl, tert.butyl and the like. This also applies to the alkyl part of "alkoxy". The term "alkylene" also embraces straight-chain and branched groups, in this case especially with 2–6 carbon atoms, e.g. 2,3-butylene or especially polymethylene such as ethylene trimethylene, tetramethylene, pentamethylene and hexamethylene.

Where an aryl group is present, it may be substituted or unsubstituted. The preferable aryl is phenyl. Phenyl may be substituted or unsubstituted (i.e., optionally substituted); however, unsubstituted phenyl is preferred. When phenyl is substituted, it is preferably substituted with one or more $C_{1-5}$-alkyl groups and/or nitro groups.

The formulae of polyenes disclosed in the scope of the present invention embrace in each case isomeric forms, e.g. optically active and cis/trans or, respectively, E/Z isomers, as well as mixtures thereof, unless expressly indicated to the contrary. The carbon atom carrying the residue $R^3$ or $R^4$ can be mentioned as an example of a chiral (optically active) centre when $R^3$ or $R^4$ is an optionally protected hydroxy group (see formulae Ia and IIa). With respect to E/Z isomerism, the all-E isomers of the educts and of the products of the process in accordance with the invention are in general preferred.

Preferably, not only $R^1$ but also $R^2$ is methyl. In this case cyclocarbonate itself is used as the reagent of formula III in order to convert the terminal formyl group(s) of the polyene aldehyde A—CHO or OHC—B—CHO into the 4-hydroxy-4-methyl-3-oxo-1-pentenyl group.

The process in accordance with the invention is conveniently carried out by reacting the polyene aldehyde with 1 to 5 equivalents of the cyclocarbonate or cyclocarbonate derivative of formula III in an organic or aqueous-organic solvent at temperatures in the range of about 25° C. to about 120° C. and in the presence of a base. All polar protic or aprotic solvents which are inert vis-à-vis the respective base which is used and, moreover, which are miscible with water are generally suitable as the organic solvent. Especially preferred solvents are lower alcohols, especially those with 1 to 3 carbon atoms, e.g. ethanol; cyclic ethers, e.g. tetrahydrofuran and dioxan; aromatics, e.g. toluene; as well as halogenated lower aliphatic hydrocarbons, e.g. methylene chloride. These organic solvents can be used in admixture with water. The base which is used can be inorganic or organic, with alkali hydroxides, e.g. sodium hydroxide and potassium hydroxide, and alkali alkoxides, preferably those which are produced from $C_{1-3}$-alkanols such as, for example, sodium ethoxide, being especially suitable. In particular, when an alkali hydroxide is used as the base an aqueous-organic reaction medium (solvent) is used. At least 2 equivalents of base, preferably from about 2.5 to about 3.5 equivalents, are conveniently used per equivalent of cyclocarbonate or cyclocarbonate derivative. As indicated above, the reaction temperatures can vary in a relatively broad range (from about 25° C. to about 120° C.); the reaction is preferably carried out at temperatures from about 40° C. to about 80° C. Moreover, the reaction is conveniently carried out at normal pressure, although in general the pressure is not critical.

After completion of the reaction the base can be neutralized by the addition of an organic or inorganic acid. Subsequently, depending on the polyene aldehyde used, the product can be isolated in a manner known per se directly by filtration or otherwise by extraction and separation of any salts present. If desired, further purification can be carried out, for example, by distillation, recrystallization etc., i.e. according to methods known per se.

The working-up is made especially simple when water-miscible solvents are used. After completion of the reaction and, where applicable, neutralization of the base 10–200% (preferably 50–150%) of water based on the amount of organic solvent used are added. The mixture is then stirred briefly or as required for several hours at temperatures between room temperature and the boiling point. In so doing not only are any salts present washed out from the crystalline product, but for the most part the conversion of a Z isomer into the desired all-E isomer takes places simultaneously. The pure product can subsequently be isolated by simple filtration, washing and drying.

Protecting groups which may be present in the product obtained can be cleaved off, if desired, also according to methods known per se, e.g. by hydrolysis with acid or base.

A number of educts used in the process in accordance with the invention are known and the production of these known educts is well documented in the technical literature (mainly that concerning carotenoids). Thus, for example, the reaction of various $C_{15}$-Wittig salts with 2,7-dimethyl-2,4,6-octatrienedial (the so-called "$C_{10}$-dialdehyde") to give the corresponding monoaldehydes of formulae Ia and Ib hereinbefore, the reaction of various $C_5$-Wittig aldehydes with long-chain polyene aldehydes also to give such monoaldehydes as well as the two-fold reaction of the $C_{10}$-dialdehyde with $C_5$- or $C_{10}$-Wittig aldehydes to give various dialdehydes of formula Ic hereinbefore, has become known from this literature. The text book "Carotenoids" (O. Isler, published by Birkhäuser, Basle and Stuttgart, 1971), especially Chapters VI and XII thereof, and the other literature referred to therein, gives many useful references to the production and the occurrence of the known educts. Where educts which have protected hydroxy, oxo or formyl groups are used, then such "protected" educts can be produced, for example, directly from the corresponding unprotected educts according to methods known per se.

The novel educts can be produced in an analogous manner to the known educts.

The reagent 4,4-dimethyl-5-methylene-1,3-dioxolan-2-one ("cyclocarbonate" itself) is a known compound, the production of which (readily from 2-methyl-3-butyn-2-ol) is described, for example, in German Patent 1,098,953 as well as in Synthesis 1981, 958–959, Bull. Chem. Soc. Japan 60, 1204–1206 (1987), Tetrahedron Lett. 30, 3981–3982 (1989) and further literature sources to which mention is made in the publication Chemistry Letters 1991, 1377–1378 (Inoue et al.) mentioned earlier. The production of not only cyclocarbonate but also of derivatives thereof is described in European Patent Publication 175,241.

Certain products of the process in accordance with the invention are novel compounds and represent a further aspect of the present invention. The novel compounds are embraced by formulae II''' and II'''' hereinafter:

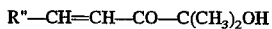   II''' wherein R" is a group (a'), (b') or (c')

and

R$^{3'}$, R$^{4'}$, m', n', p', q' and r' have the significances of R$^3$, R$^4$, m, n, p,q and, respectively, r given above and R$^{5'}$ is either the 4-hydroxy-4-methyl-3-oxo-1-pentenyl group, the formyl group or a protected formyl group, and with the provisos that (i) with respect to group (a') m' is other than 2 or 3 when simultaneously R$^{3'}$ is hydrogen or an optionally protected oxo group, R$^{4'}$ is hydrogen and n' is 0; and m' is other than 3 when simultaneously R$^{3'}$ is an optionally protected hydroxy group, R$^{4'}$ is hydrogen or an optionally protected oxo group and n' is 0;

(ii) with respect to group (b') q' is other than 3 when p' is 2 and n' is 0; and (iii) with respect to group (c') r' is other than 2 when n' is 0.

$$R'''—CH=CH—CO—CR^{1'}R^{2'}OH \qquad II''''$$

wherein

R''' has the significance of R given above, with the formyl group either being free (unprotected), being protected or being replaced by the —CH=CH—CO—R$^{1'}$R$^{2'}$OH group when R''' is group (c), and R$^{1'}$ and R$^{2'}$ have the significances of R$^1$ and R$^2$ given above, with the proviso that at least one of R$^{1'}$ and R$^{2'}$ is other than methyl.

Included among the novel compounds are

13'-hydroxy-13',14'-dihydro-12'-apo-β-caroten-14'-one,

9'-hydroxy-9',10'-dihydro-8'-apo-β-caroten-10'-one, (all-E)-2-hydroxy-2,6,10,14,18,23,27-heptamethyl-29-(2,6,6-trimethyl-cyclohex-1-enyl)-nonacosa-4,6,8,10,12,14, 16,18,20,22,24,26,28-tridecaen-3-one, 7'-hydroxy-7'-methyl-7',8'-dihydro-9'-nor-6'-apo-β-caroten-8'-one, 5,5'-dihydroxy-5,6,5',6'-tetrahydro-4,4'-diapo-ψ,ψ-carotene-6,6'-dione, 2-hydroxy-2,6,11,15-tetramethyl-17-(2,6,6-trimethyl-3-oxo-cyclohex-1-enyl)-heptadeca-4,6,8,10,12,14,16-heptaen-3-one, 2-hydroxy-17-(4R-hydroxy-2,6,6-trimethyl-cyclohex-1-enyl)-2,6,11,15-tetramethyl-heptadeca-4,6,8,10,12,14, 16-heptaen-3-one, 2-hydroxy-25-(4R-hydroxy-2,6,6-trimethyl-cyclohex-1-enyl)-2,6,10,14,19,23-hexamethyl-pentacosa-4,6,8,10, 12,14, 16,18,20,22,24-undecaen-3-one, (4E,6E,8E,10E,12E,14E,16E,18E)-2-hydroxy-2,6,11,15, 19, 23-hexamethyl-tetracosa-4,6,8,10,12,14,16,18,22-nonaen-3-one, all-E-(R/S)-3-hydroxy-3,7,11,15,20,24-hexamethyl-26-(2,6,6-trimethyl-cyclohex-1-enyl)-hexacosa-5,7,9,11, 13,15,17, 19,21,23,25-undecaen-4-one, 3-ethyl-3-hydroxy-7,11,15,20,24-pentamethyl-26-(2,6,6-trimethyl-cycohex-1-enyl)-hexacosa-5,7,9,11,13,15, 17,19,21, 23,25-undecaen-4-one and 1'-hydroxy-16'-(3-methylbut-2-enyl)-1',2'-dihydrobeta-χ-caroten-2'-one.

The products of the process in accordance with the invention belong for the most part to the carotenoid field and are used correspondingly, for example as colorants or pigments for foodstuffs, egg yolk, integuments (especially skin, legs and beaks) and/or the subcutaneous fat of poultry, the flesh and/or the integuments (especially skin, scales and shell) of fish and crustaceans etc. This use can be effected according to methods known per se, as described, for example, in European Patent Publication No. 630,578.

The use of the novel products represents a further aspect of the present invention.

The invention is illustrated by the following Examples:

EXAMPLE 1

Reaction of vitamin A aldehyde with cyclocarbonate to give 13'-hydroxy-13',14'-dihydro-12'-apo-β-caroten-14'-one 4.97 g (0.0175 mol) of vitamin A aldehyde are suspended in 50 ml of n-propanol under argon in a 200 ml sulphonation flask fitted with a stirrer, thermometer, condenser and dropping funnel. 7.82 g (0.060 mol) of cyclocarbonate are introduced by rinsing with 20 ml of n-propanol into the resulting yellow solution. Then, 9.6 ml of 50% potassium hydroxide solution are added dropwise to the yellow solution within one minute. In so doing the temperature rises to 51° C. The solution becomes turbid and firstly dark orange, then brownish in colour. The mixture is heated to 70° C. in an oil bath. A white precipitate is deposited on the wall of the flask. According to thin-layer chromatography the reaction has almost finished already after one hour. After a further two hours the orange-brown, turbid reaction mixture is cooled to room temperature using a water bath.

For the working-up, 50 ml of semi-saturated sodium chloride solution are added to the mixture and it is stirred vigorously for two minutes. Subsequently, the mixture is rinsed with 30 ml of n-propanol into a 250 ml separating funnel and the phases are left to separate. The aqueous phase is separated off and the organic phase is extracted three times with 50 ml of semi-saturated sodium chloride solution each time, with the last aqueous phase having a pH value of about 6. The combined aqueous phases are then back-extracted twice with 25 ml of n-propanol each time. After drying the combined organic phases over anhydrous sodium sulphate these are concentrated completely under reduced pressure at 50° C. An orange-red, in part crystal-line oil remains behind. In this manner there is obtained 13'-hydroxy-13',14'-dihydro-12'-apo-β-caroten-14'-one (7.1 g) in crude state, with the yield of the desired product presumably being almost 100%.

$^1$H-NMR [CDCl$_3$, tetramethylsilane (TMS) as internal standard]: δ=1.03 ppm (s,6H), 1.40 ppm (s,6H), 4.11 ppm (s, 1H), 7.86–7.93 ppm (m,1H).

EXAMPLE 2

Reaction of β-apo-12'-carotenal with cyclocarbonate to give 9',10'-dihydro-8'-apo-β-caroten-10'-one 7.01 g (0.020 mol) of β-apo-12'-carotenal are suspended in 30 ml of ethanol under argon in a 200 ml sulphonation flask fitted with a stirrer, thermometer, condenser and dropping funnel. 7.82 g (0.060 mol) of cyclocarbonate are introduced by rinsing with 20 ml of ethanol into the resulting dark red suspension, and subsequently 10.3 ml of 50% potassium hydroxide solution are added dropwise within 5 minutes. In so doing the mixture is cooled slightly from time to time in a water bath in order that the temperature does not exceed 50° C. The orange-brown suspension is heated to 50° C. A white precipitate is deposited on the flask wall and orange flecks also appear on the flask wall after a short time. The reaction is followed by thin-layer chromatography and HPLC, according to which the reaction has almost finished after 3.5 hours. The resulting orange-red suspension is cooled in an ice/water bath to 3° C. and stirred at this temperature for a further hour. Then, it is filtered and the crystallizate is washed three times with 50 ml of water each time and thereafter dried at 50° C. for 16 hours under reduced pressure. In this manner there are obtained 7.69 g of 9'-hydroxy-9',10'-dihydro-8'-apo-β-caroten-10'-one as a red crystallizate. The yield corresponds to about 88.5% of theory.

$^1$H-NMR (CDCl$_3$, TMS as the internal standard): δ=1.04 ppm (s,6H), 1.42 ppm (s,6H), 1.72 ppm (s,3H), 1.96–2.02 ppm (m,11H), 4.10 ppm (s,1H), 6.12–6.29 ppm (m,6H), 6.61–6.88 ppm (m,4H), 7.54–7.58 ppm (d,1H).

EXAMPLE 3

Reaction of β-apo-8'-carotenal with cyclocarbonate to give 5'-hydroxy-5',6'-dihydro-4'-apo-β-caroten-6'-one 10.00 g (0.024 mol) of β-apo-8'-carotenal are suspended in 80 ml of dioxan under argon in a 350 ml sulphonation flask fitted with a stirrer, thermometer, condenser and dropping funnel. 9.30 g (0.072 mol) of cyclocarbonate are introduced by rinsing with 20 ml of dioxan into the resulting thin suspension, and subsequently 12.45 ml of 50% potassium hydroxide solution are added dropwise within 20 minutes. The mixture is then heated using a water bath to the reflux temperature (about 100° C.) and after 22 hours 3.8% of educt are still present in the reaction mixture according to thin-layer chromatography and HPLC. About 50 ml of dioxan are distilled off at normal pressure, whereafter so the oil bath is removed. 150 ml of n-propanol and 100 ml of water are added to the mixture, whereupon brownish crystals are precipitated. Subsequently, the reaction mixture is again heated to the reflux temperature (about 80° C.) and stirred at this temperature for 30 minutes, thereafter cooled to room temperature and stirred at this temperature for 15 minutes. After filtering off the violet crystals these are rinsed twice with 50 ml of n-propanol each time and subsequently three times with 50 ml of water each time, finally dried for 16 hours under reduced pressure (20 mbar) at about 60° C. In this manner there are obtained 6.88 g (yield about 57.2% of theory) of 5'-hydroxy-5',6'-dihydro-4'-apo-β-caroten-6'-one as fine violet crystals.

$^1$H-NMR (CDCl$_3$, TMS as internal standard): δ=1.03 ppm (s,6H), 1.43 ppm (s,6H), 1.46–1.48 ppm (m,2H), 1.60–1.63 ppm (m,2H), 1.72 ppm (s,3H), 1.98–2.04 ppm (m, 14H), 4.09 ppm (s broad, 1H), 6.14–6.73 ppm (m, 13H), 7.55+7.59 ppm (d,1H).

EXAMPLE 4

Reaction of β-apo-4'-carotenal with cyclocarbonate to give 2'-dehydroplectaniaxanthin 10.12 g of β-apo-4'-carotenal are suspended in 50 ml of n-propanol under argon in a 350 ml sulphonation flask fitted with a stirrer, thermometer, cooler and dosage pump. Then, 9.6 ml of 50% potassium hydroxide solution are added. The red-violet, thin suspension is now heated to 70° C. internal temperature. Then, a solution of 7.72 g of cyclocarbonate in 20 ml of n-propanol is dosed in using the dosage pump within one hour at 70° C. The mixture is stirred at 70° C. for 5 hours under control by thin-layer chromatography and HPLC. Almost all of the β-apo-4'-carotenal has reacted after this time according to HPLC. 70 ml of water are added to the mixture and the red-brown, thin reaction mixture is heated to reflux and stirred at an internal temperature of 89.3° C. Thereafter, the oil bath is removed and the mixture is cooled to 22° C. using a water bath and stirred for 30 minutes. The crystals are subsequently filtered off under suction and washed in succession twice with 50 ml of n-propanol each time and three times with 50 ml of water each time. After filtering off the crystals these are dried for 16 hours at 50° C. under reduced pressure. In this manner there are obtained 11.09 g (97.8% of theory) of 2'-dehydroplectaniaxanthin as brown crystals.

$^1$H-NMR (CDCl$_3$, TMS as internal standard): δ=1.03 ppm (s,6H), 1.43 ppm (s,6H), 1.72 ppm (s,3H), 1.98–2.03 ppm (m,17H), 4.14 ppm (s,1H), 6.11–6.24 ppm (m,3H), 6.27–6.47 ppm (m,6H), 7.55+7.59 ppm (d, 1H).

EXAMPLE 5

Reaction of torularhodinaldehyde with cyclocarbonate to give (all-E)-2-hydroxy-2,6,10,14, 18,23,27-heptamethyl-29-(2,6,6-trimethyl-cyclohexy-1-enyl)-nonacosa-4,6,8,10,12,14,16,18, 20, 22,24,26,28-tridecaen-3-one 24.3 ml of 50% aqueous potassium hydroxide solution are added dropwise within one minute while stirring to a mixture of 20.00 g of torularhodinaldehyde and 18.79 g of cyclocarbonate in 200 ml of n-propanol in a 750 ml sulphonation flask fitted with a stirrer, thermometer, condenser and dropping funnel, the temperature rising to 50° C. The reaction mixture is heated to the reflux temperature (about 90° C.) and the course of the reaction is followed by HPLC. After 2.5 hours it is established that 1.8% of educt are still present, whereupon the reaction is provisionally interrupted by adding 200 ml of water and subsequently heated to the reflux temperature (about 90° C.) for a further hour. Thereafter, the resulting suspension is cooled to 25° C. and the crystallizate is filtered off and washed in sequence twice with 100 ml of n-propanol each time and three times with 100 ml of water each time. The resulting black crystallizate is dried for 16 hours at 50° C. and under reduced pressure. This gives 21.7 g of crude product.

In order to purify the crude crystallizate, 19.31 g thereof are dissolved in 380 ml of methylene chloride at 25° C. 380 ml of methanol are then added dropwise to the solution within one hour while stirring, whereby glistening dark-violet crystals are precipitated. After stirring at 25° C. for one hour the crystals are filtered off and washed twice with 60 ml of methanol/methylene chloride (2:1) each time. The crystals are purified a second time in this manner and they are subsequently dried for 16 hours at 50° C. and under reduced pressure. In this manner there are obtained 14.7 g (63.7% of theory) of (all-E)-2-hydroxy-2,6,10, 14,18,23,27-heptamethyl-29-(2,6,6-trimethyl-cyclohex-1-enyl)-nonacosa-4,6,8,10,12,14,16,18,20,22,24,26,28-tridecaen-3-one as dark brown crystals.

$^1$H-NMR (CDCl$_3$, TMS as internal standard): δ=1.03 ppm (s,6H), 1.43 ppm (s,6H), 1.44–1.48 ppm (m, 2H), 1.58–1.65 ppm (m,2H), 1.72 ppm (s,3H), 2.00–2.04 ppm (m,20H), 4.11 ppm (s broad, 1H), 6.11–6.17 ppm (m,3H), 6.21–6.49 ppm (m,8H), 6.58–6.70 ppm (m,7H), 7.55+7.59 ppm (d,1H).

EXAMPLE 6

Reaction of β-apo-10'-carotenal with cyclocarbonate to give 7'-hydroxy-7'-methyl-7',8'-dihydro-9'-nor-6'-apo-β-caroten-8'-one 7.53 g (0.020 mol) of β-apo-10'-carotenal are suspended in 50 ml of n-propanol under argon in a 350 ml sulphonation flask fitted with a stirrer, thermometer, condenser and dropping funnel. 7.82 g (0.060 mol) of cyclocarbonate are introduced by rinsing with 20 ml of n-propanol into the resulting dark red-brown suspension, and subsequently 9.6 ml of 50% potassium hydroxide solution are added dropwise within 2 minutes. In so doing the temperature rises to 46° C. The reaction mixture is heated to 70° C., whereafter a white precipitate is deposited on the flask wall. The reaction has almost finished after 2.5 hours according to thin-layer chromatography. The mixture is cooled to 0° C. using ice bath cooling and is subsequently stirred for 3 hours. Then, the resulting crystals are filtered off under suction and washed in sequence with 50 ml of n-propanol and three times with 50 ml of water each time. Finally, the crystallizate is dried for about 16 hours at 50° C. and under reduced pressure. In this manner there are obtained 5.83 g (63.3% of theory) of 7'-hydroxy-7'-methyl-7',8'-dihydro-9'-nor-6'-apo-β-caroten-8'-one as wine red-violet crystals.

$^1$H-NMR (CDCl$_3$, TMS as internal standard): δ=1.03 ppm (s,6H), 1.41 ppm (s,6H), 1.45–1.48 ppm (m, 2H), 1.60–1.63 ppm (m,2H), 1.72 ppm (s,3H), 1.95–2.02 ppm (m, 11H), 6.12–6.49 ppm (m, 8H), 6.58–6.78 ppm (m,4H), 7.53–7.59 ppm (m, 1H).

EXAMPLE 7

Reaction of crocetin dialdehyde with cyclocarbonate to give 5,5'-dihydroxy-5,6,5',6'-tetrahydro-4,4'-diapo-ψ,ψ-carotene-6,6'-dione 5.04 g (0.0170 mol) of crocetin dialdehyde are suspended in 20 ml of n-propanol under argon in a 200 ml sulphonation flask fitted with a stirrer, thermometer, condenser and dropping funnel. 13.15 g (0.102 mol) of cyclocarbonate are introduced by rinsing with 5 ml of n-propanol into the resulting orange-red suspension, and subsequently 16.25 ml of 50% potassium hydroxide solution are added dropwise within 15 minutes. In so doing the temperature rises to about 68° C. The mixture is cooled slightly from time to time in an ice bath in order that the temperature does not exceed 70° C. During the addition of the potassium hydroxide solution the colour of the mixture changes from orange-red to red. Thereafter, the mixture is heated to 70° C. and stirred at this temperature for a further 1.25 hours. After this reaction 50 ml of water are added and the reaction mixture is stirred at 70° C. for a further hour. The mixture is again cooled to room temperature and the resulting crystal slurry is suction filtered and washed twice with 15 ml of n-propanol each time and three times with 20 ml of water each time. The red-violet crystals are dried for 16 hours at 50° C. under reduced pressure at 20–30 mbar. In this manner there are obtained 7.07 g (89.5% of theory) of 5,5'-dihydroxy-5,6,5',6'-tetrahydro-4,4'-diapo-ψ,ψ-carotene-6,6'-dione as red-violet crystals.

$^1$H-NMR (CDCl$_3$, TMS as internal standard): δ=1.43 ppm (s,12H), 1.99 ppm (s,12H), 4.10 ppm (s,2H), 6.38–6.73 ppm (m,12H), 7.54+7.58 ppm (d,2H).

EXAMPLE 8

Reaction of diapo-4,4'-carotenedial with cyclocarbonate to give phillipsiaxanthin 3.00 g (0.0070 mol) of diapo-4,4'-carotenedial are suspended in 20 ml of n-propanol under argon in a 100 ml sulphonation flask fitted with a stirrer, thermometer, condenser and dropping funnel. 5.41 g (0.042 mol) of cyclocarbonate are introduced by rinsing with 5 ml of n-propanol into the resulting orange-red suspension, and subsequently 6.70 ml of 50% potassium hydroxide solution are added dropwise within 15 minutes. In so doing, the temperature rises to about 68° C. The mixture is cooled slightly from time to time in an ice bath in order that the temperature does not exceed 70° C. During the addition of the potassium hydroxide solution the colour of the mixture changes from red to red-brown. Thereafter, the mixture is heated to 70° C. using an oil bath and is stirred at this temperature for about a further 23 hours, during which time the reaction has still not finished according to thin-layer chromatography and HPLC. The oil bath is removed and the reaction mixture is cooled to about 50° C. Subsequently, a further 1.80 g (0.014 mol) of cyclocarbonate as well as 2.32 ml of 50% potassium hydroxide solution are added to the reaction mixture within 2 minutes, the temperature of the reaction mixture again rising to about 65° C. The mixture is stirred at 70° C. for a further 1.25 hours, 50 ml of water are added thereto and the mixture obtained is stirred at 70° C. for a further hour. The mixture is again cooled to room temperature and the resulting red-brown crystal slurry is suction filtered and washed twice with 15 ml of n-propanol each time and three times with 20 ml of water each time. The dark violet crystals are dried for 16 hours at 50° C. under reduced pressure and 20–30 mbar. In this manner there are obtained 3.22 g (76.8% of theory) of phillipsiaxanthin as dark violet crystals.

$^1$H-NMR (CDCl$_3$, TMS as internal standard): δ=1.43 ppm (s,12H), 1.99 ppm (s,12H), 2.01 ppm (s,6H), 4.12 ppm (s,2H), 6.32–6.48 ppm (m, 8H), 6.59–6.69 ppm (m, 10H), 7.54+7.58 ppm (d,2H).

EXAMPLE 9

Reaction of β-apo-12'-canthaxanthinal with cyclocarbonate to give 2-hydroxy-2,6,11,15-tetramethyl-17-(2,6,6-trimethyl-3-oxo-cyclohex-1-enyl)-heptadeca-4,6,8,10,12,14,16-heptaen-3-one 1.50 g (0.0041 mol) of β-apo-12'-canthaxanthinal are suspended in 15 ml of methanol under argon in a 100 ml sulphonation flask fitted with a stirrer, thermometer, condenser and dropping funnel. 1.59 g (0.0124 mol) of cyclocarbonate are introduced by rinsing with 6 ml of methanol into the resulting suspension, and subsequently 5.26 ml of 30% sodium methylate solution are added dropwise within 3 minutes while stirring. In so doing the temperature rises slowly to 35° C. The reaction mixture is heated to 50° C. in an oil bath and stirred under control by thin-layer chromatography and HPLC. After 5 hours at 50° C. the resulting red suspension is heated to reflux temperature (65° C.), with the suspension becoming dark red and relatively thin. It is stirred at reflux temperature for 2.5 hours and subsequently cooled to room temperature. The suspension, which has again become red, is stirred at this temperature for 16 hours. 29 ml of water are then added and the mixture is heated for a further 5 hours at reflux temperature (78° C.) with constant stirring. A pale red suspension is thereby obtained. This is then cooled to room temperature, stirred for one hour and finally filtered, and the crude reaction product isolated in this manner is washed twice at −20° C. with 2 ml of methanol each time and three times with 2 ml of water each time and dried for about 16 hours at 45° C. under reduced pressure (vacuum drying oven).

In this manner there are obtained 1.56 g of 2-hydroxy-2, 6,11,15-tetramethyl-17-(2,6,6-trimethyl-3-oxo-cyclohex-1-enyl)-heptadeca-4,6,8,10,12,14,16-heptaen-3-one as red crystals. The yield corresponds to about 84.4% of theory.

$^1$H-NMR (CDCl$_3$, TMS as internal standard): δ=1.20 ppm (s,6H), 1.43 ppm (s,6H), 1.84–1.87 ppm (m,5H), 1.98 ppm (s,3H), 2.02 ppm (s,6H), 2.49–2.53 ppm (t,2H), 4.09 ppm (s,1H), 6.25–6.50 ppm (m,6H), 6.64–6.90 ppm (m,4H), 7.54+7.58 ppm (d,1H).

EXAMPLE 10

Reaction of β-apo-12'-zeaxanthinal with cyclocarbonate to give 2-hydroxy-17-(4R-hydroxy-2,6,6-trimethyl-cyclohex-1-enyl)-2,6,11,15-tetramethyl-heptadeca-4,6,8,10,12,14,16-heptaen-3-one 1.83 g (0.0050 mol) of β-apo-12'-zeaxanthinal are suspended in 15 ml of isopropanol under argon in a 100 ml sulphonation flask fitted with a stirrer, thermometer and condenser. 1.93 g of cyclocarbonate are introduced by rinsing with 10 ml of isopropanol into the resulting suspension, and subsequently 2.58 ml of 50% potassium hydroxide solution are added dropwise at 15° C. using a pipette in such a manner that the temperature does not exceed 22° C. After reaction at room temperature for 18 hours the reaction mixture (red suspension) still contains a relatively large amount of educt and, accordingly, a further 1.29 g of cyclocarbonate (total amount 0.0250 mol) together with a small amount of isopropanol are added. Furthermore, with the reaction mixture at a temperature of 15° C. 1.47 ml of 50% potassium hydroxide solution are added dropwise in such a manner that the temperature does not exceed 22° C. After reaction at room temperature for a further 2.75 hours, after which the amount of unreacted educt no longer decreases, 35 ml of deionized water are added within one minute. Thereby, the temperature rises to about 27° C. and orange crystals are precipitated. The suspension is stirred at room temperature for a further one and a half hours, subsequently suction filtered and the crystallizate obtained is washed twice at 0° C. with 6 ml of isopropanol each time and three times with 6 ml of deionized water each time. Finally, the crystals are dried for about 16 hours at 50° C. under reduced pressure (vacuum drying oven).

In this manner there are obtained 1.51 g of 2-hydroxy-17-(4R-hydroxy-2,6,6-trimethyl-cyclohex-1-enyl)-2,6,11, 15-tetramethyl-heptadeca- 4,6,8,10,12,14,16-heptaen-3-one as orange crystals. The yield corresponds to about 67.0% of theory.

$^1$H-NMR (CDCl$_3$, TMS as internal standard): δ=1.08 ppm (s,6H), 1.42–1.51 ppm (m,7H), 1.74–1.79 ppm (m,4H), 1.97–2.08 ppm (m,10H), 2.36–2.42 ppm (m,2H), 4.00 ppm (m,1H), 4.10 ppm (s,1H), 6.14–6.44 ppm (m,6H), 6.58–6.88 ppm (m,4H), 7.54+7.58 ppm (d,1H).

EXAMPLE 11

Reaction of β-apo-4'-zeaxanthinal with cyclocarbonate to give 2-hydroxy-25-(4R-hydroxy-2,6,6-trimethyl-cyclohex-1-enyl)-2,6,10,14,19,23-hexamethyl-pentacosa-4,6,8,10,12,14,16,18,20, 22, 24-undecaen-3-one 1.78 g (0.0036 mol) of β-apo-4'-zeaxanthinal are suspended in 15 ml of ethanol under argon in a 100 ml sulphonation flask fitted with a stirrer, thermometer and condenser. 1.38 g (0.0107 mol) of cyclocarbonate are introduced by rinsing with 10 ml of ethanol into the resulting suspension, and subsequently 1.84 ml of 50% potassium hydroxide solution are added dropwise within one minute. In so doing the temperature rises to about 44° C. The reaction mixture is heated to reflux temperature (78° C.) using an oil bath and stirred for 4 hours under control by thin-layer chromatography and HPLC. Then, 35 ml of water are added within one minute, with the temperature dropping to about 53° C. and large red-brown crystals being precipitated. The mixture is heated at reflux temperature (about 81° C.) for a further hour in order to isomerise the product. Subsequently, the oil bath is replaced by a water bath and the mixture is cooled to room temperature. After stirring for about one hour the crystals are filtered off under suction and washed twice at 0° C. with 6 ml of ethanol each time and three times with 6 ml of water each time. Finally, the dark brown crystals obtained are dried for about 16 hours at 50° C. under reduced pressure (vacuum drying oven).

In this manner there are obtained 1.80 g of 2-hydroxy-25-(4R-hydroxy-2,6,6-trimethyl-cyclohex-1-enyl)-2,6,10, 14,19,23-hexamethyl-pentacosa-4,6,8,10,12,14,16,18,20, 22,24-undecaen- 3-one as dark brown crystals. The yield corresponds to about 86.5% of theory.

$^1$H-NMR (CDCl$_3$, TMS as internal standard): δ=1.08 ppm (s,6H), 1.43–1.51 ppm (m,8H), 1.74–1.79 ppm (m,4H), 1.98–2.08 ppm (m,16H), 2.36–2.42 ppm (m,1H), 3.99 ppm (m,1H), 4.13 ppm (s,1H), 6.13–6.17 ppm (m,3H), 6.25–6.48 ppm (m,6H), 6.59–6.71 ppm (m,7H), 7.55+7.58 ppm (d,1H).

EXAMPLE 12

Reaction of apo-12'-lycopenal with cyclocarbonate to give (4E,6E,8E,10E,12E, 14E,16E,18E)-2-hydroxy-2,6,11,15,19,23-hexamethyl-tetracosa-4,6, 8,10,12,14,16,18,22-nonaen-3-one 14.20 g (0.0405 mol) of apo-12'-lycopenal are suspended in 50 ml of propanol under argon in a 500 ml sulphonation flask fitted with a stirrer, thermometer, condenser and dropping funnel. 10.44 g (0.081 moll of cyclocarbonate are introduced by rinsing with 72 ml of propanol into the resulting suspension, and subsequently 15.0 ml of 50% potassium hydroxide solution are added dropwise within one minute while stirring. In so doing the temperature rises to about 42° C. Then, the reaction mixture is heated to 70° C.

using an oil bath and is stirred under control by thin-layer chromatography and HPLC. After a reaction time at 70° C. of about 2 hours 170 ml of water are added. The resulting orange-brown, glistening suspension is again heated to 70° C. and stirred for a further hour. Subsequently, the mixture is cooled to about 25° C. in a water bath, stirred for 2 hours and filtered over a sintered glass filter under suction. The crystal cake is pressed solid, washed in sequence twice with 35 ml of propanol each time and three times with 35 ml of water each time, with suction filtration being carried out and the crystal cake being pressed solid between the washing operations, and is dried for about 16 hours at 50° C. under reduced pressure (vacuum drying oven).

In this manner there are obtained 14.81 g of (4E,6E,8E,10E, 12E,14E,16E,18E)-2-hydroxy-2,6,11,15,19,23-hexamethyltetracosa- 4,6,8,10,12,14,16,18,22-nonaen-3-one as copper-orange, glistening crystals. The yield corresponds to about 84.1% of theory.

$^1$H-NMR (CDCl$_3$, TMS as internal standard): δ=1.42 ppm (s,6H), 1.62 ppm (s,3H), 1.69 ppm (s,3H), 1.83 ppm (s,3H), 1.97 ppm (s,3H), 1.98 ppm (s,3H), 2.02 ppm (s,3H), 2.12 ppm (s,4H), 4.11 ppm (s,1H), 5.11 ppm (s, 1H), 5.94+5.97 ppm (d,1H), 6.18–6.84 ppm (m,10H), 7.54+7.58 ppm (d,1H).

EXAMPLE 13

Reaction of apo-4'-lycopenal with cyclocarbonate to give all-E-3,4-didehydro-1,2-dihydro-1-hydroxy-ψ,ψ-caroten-2-one 13.50 g (0.028 mol) of apo-4'-lycopenal are suspended in 80 ml of propanol under argon in a 500 ml sulphonation flask fitted with a stirrer, thermometer, condenser and dropping funnel. 10.81 g (0.084 mol) of cyclocarbonate are introduced by rinsing with 60 ml of propanol into the resulting suspension, and subsequently 14.5 ml of 50% potassium hydroxide solution are added dropwise within 3 minutes while stirring. In so doing the temperature rises to about 43° C. The reaction mixture is then heated to reflux temperature (93° C.) using an oil bath and stirred under control by thin-layer chromatography and HPLC. After a reaction time at reflux temperature of about 2 hours 200 ml of water are added. The resulting brown suspension is again heated to reflux temperature (88° C.) and stirred for a further hour. Subsequently, the mixture is cooled to about 25° C., stirred for 2.5 hours and filtered over a sintered glass filter under suction. The crystal cake is pressed solid, washed in sequence twice with 70 ml of propanol each time and three times with 70 ml of water each time, with suction filtration being carried out and the crystal cake being pressed solid between the washing operations, and dried for about 16 hours at 50° C. under reduced pressure (vacuum drying oven).

In this manner there are obtained 15.00 g of all-E-3,4-didehydro-1,2-dihydro-1-hydroxy-ψ,ψ-caroten-2-one as brown crystals. The yield corresponds to 94.6% of theory, although the product requires a further purification.

For the purpose of purification, 14.78 g of the product are suspended in 150 ml of methylene chloride while stirring. Then, the resulting suspension is heated in an oil bath to reflux temperature and is stirred at this temperature for 15 minutes. The crystals do not dissolve. The suspension is cooled in a water bath to room temperature, stirred at this temperature for one hour and suction filtered over a sintered glass filter. The crystals obtained are washed twice with 25 ml of methylene chloride each time and the resulting black, glistening crystals are dried for about 16 hours at 50° C. under reduced pressure (vacuum drying oven).

In this manner there are obtained 12.77 g (81.8% of theory) of pure all-E-3,4-didehydro-1,2-dihydro-1-hydroxy-ψ,ψ-caroten-2-one as black crystals.

$^1$H-NMR (CDCl$_3$, TMS as internal standard): δ=1.43 ppm (s,6H), 1.61 ppm (s,3H), 1.69 ppm (s,3H), 1.82 ppm (s,3H), 1.98 ppm (s,12H), 2.00 ppm (s,3H), 2.12 ppm (s,4H), 4.12 ppm (s,1H), 5.11 ppm (s, 1H), 5.94+5.97 ppm (d,1H), 6.20–6.65 ppm (m,16H), 7.55+7.59 ppm (d,1H).

EXAMPLE 14

Reaction of β-apo-4'-carotenal with 4-ethyl-4-methyl-5-methylene-1,3-dioxolan-2-one to give all-E-(R/S)-3-hydroxy-3,7,11,15,20,24-hexamethyl-26-(2,6,6-trimethyl-cyclohex-1-enyl)-hexacosa-5,7,9,11,13,15,17,19,21,23,25-undecaen-4-one 4.96 g (0.01 mol) of β-apo-4'-carotenal are suspended in 20 ml of isopropanol under argon in a 100 ml sulphonation flask fitted with a stirrer, thermometer, condenser and dropping funnel. 5.68 g (0.040 mol) of 4-ethyl-4-methyl-5-methylene-1,3-dioxolan-2-one are introduced by rinsing with 5 ml of isopropanol into the resulting suspension, and subsequently 6.47 ml of 50% potassium hydroxide solution are added dropwise within 10 minutes while stirring. In so doing the temperature rises to about 57° C. The blood-red suspension is then heated to 80° C. using an oil bath, with the colour changing to copper-like. After a total reaction time of 4.5 hours, 25 ml of water are added to the batch. The brown-red suspension is again heated to 80° C. and is stirred at this temperature for a further hour. Subsequently, it is cooled using a water bath to room temperature (21° C.) and stirred at this temperature for 30 minutes. Then, the glistening, grey crystals are filtered off under suction, washed twice with 25 ml of isopropanol each time and three times with 25 ml of water each time and dried for about 16 hours at 50° C. under reduced pressure (vacuum drying oven).

In this manner there are obtained 5.35 g of all-E-(R/S)-3-hydroxy-3,7,11,15,20,24-hexamethyl-26-(2,6,6-trimethyl-cyclohex-1-enyl)-hexacosa-5,7,9,11,13,15,17,19,21,23,25-undecaen-4-one as violet crystals. The yield corresponds to about 92.1% of theory, although the product requires a further purification; this is effected by repeated recrystallization from a mixture of methylene chloride and methanol, with the remaining educt being separate each time.

$^1$H-NMR (CDCl$_3$, TMS as internal standard): δ=0.80–0.84 ppm (t,3H), 1.03 ppm (s,6H), 1.39 ppm (s,3H), 1.45–1.48 ppm (m,2H), 1.59–1.65 ppm (m,2H), 1.72 ppm (s,3H), 1.74–1.84 ppm (m,2H), 1.97–2.04 ppm (m,17H), 4.14 ppm (s,1H), 6.11–6.47 ppm (m,9H), 6.54–6.71 ppm (m,7H), 7.55+7.58 ppm (d,1H).

EXAMPLE 15

Reaction of β-apo-4'-carotenal with 4,4-diethyl-5-methylene-1,3-dioxolan-2-one to give 3-ethyl-3-hydroxy-7,11,15,20,24-pentamethyl-26-(2,6,6-trimethyl-cyclohex-1-enyl)-hexacosa-5,7,9,11,13,15,17,19,21,23,25-undecaen-4-one 10.00 g (0.0202 mol) of β-apo-4'-carotenal are suspended in 30 ml of propanol under argon in a 200 ml sulphonation flask fitted with a stirrer, thermometer, condenser and dropping funnel. 6.53 g (0.0403 mol) of 4,4-diethyl-5- methylene-1,3-dioxolan- 2-one are introduced by rinsing with 20 ml of propanol into the resulting suspension, and subsequently 7.52 ml of 50% potassium hydroxide solution are added dropwise within one minute while stirring. In so doing the temperature rises to about 47° C. The violet-red suspension is then heated to 80° C. using an oil bath. After a reaction time of 5 hours 70 ml of deionized water are added to the reaction mixture, whereupon it is again heated to 80° C. and stirred at this temperature for a further one hour. Subsequently, it is cooled to 25° C. using a water bath and stirred at this temperature for 30 minutes. Then, the suspension is suction filtered over a slotted glass suction filter fitted with a paper filter, the crystal cake obtained is pressed solid and washed twice with 50 ml of propanol each time and three times with 50 ml of deionized water each time, with suction filtration being carried out and the crystal cake being pressed solid between the washing operations, and finally dried for about 16 hours at 50° C. under reduced pressure (vacuum drying oven).

In this manner there are obtained 11.96 g of 3-ethyl-3-hydroxy-7,11,15,20,24-pentamethyl-26-(2,6,6-trimethylcyclohex-1-enyl)-hexacosa-5,7,9,11,13,15,17,19,21,23,25-undecaen-4-one as brown crystals. The yield corresponds to about 99.0% of theory.

$^1$H-NMR (CDCl$_3$, TMS as internal standard): δ=0.77+0.79+0.81 ppm (t,6H), 1.05 ppm (s,6H), 1.45–1.48 ppm (m,2H), 1.58–1.64 ppm (m,2H), 1.72 ppm (s,3H), 1.73–1.78 ppm (m,4H), 1.98–2.02 ppm (m, 17H), 4.13 ppm (s, 1H), 6.11–6.21 ppm (m,3H), 6.25+6.27 ppm (d,1H), 6.31–6.40 ppm (m,4H), 6.44+6.48 ppm (d,1H), 6.56–6.72 ppm (m,7H), 7.55+7.59 ppm (d,1H).

EXAMPLE 16

Reaction of β-apo-4'-carotenal with 4-methyl-4-(4-methyl-3-pentenyl)-5-methylene-1,3-dioxolan-2-one to give 1'-hydroxy-16'-(3-methylbut-2-enyl)-1',2'-dihydrobeta-χ-caroten-2'-one 19.84 g (0.040 mol) of β-apo-4'-carotenal are suspended in 60 ml of isopropanol under argon in a 200 ml sulphonation flask fitted with a stirrer, thermometer, condenser and dropping funnel. 16.53 g of 4-methyl-4-(4-methyl-3-pentenyl)-5-methylene-1,3-dioxolan-2-one are introduced by rinsing with 40 ml of isopropanol into the resulting suspension, and subsequently 14.81 ml of 50% potassium hydroxide solution are added dropwise within 2 minutes while stirring. In so doing the temperature rises to about 46° C. The violet-red suspension is then heated to 70° C. using an oil bath. After a reaction time of 4.75 hours 140 ml of water are added to the reaction mixture, whereupon it is again heated to 70° C. and stirred at this temperature for a further hour. Subsequently, it is cooled using a water bath to 25° C. and stirred at this temperature for 15 minutes. Then, the crystals are filtered off, the crystal cake obtained is pressed solid and washed twice with 100 ml of isopropanol each time and three times with 100 ml of water each time, with suction filtration being carried out and the crystal cake being pressed solid between the washing operations, and finally dried for about 16 hours at 50° C. under reduced pressure (vacuum drying oven).

In this manner there are obtained 23.38 g of 1'-hydroxy-16'-(3-methylbut-2-enyl)-1',2'-dihydrobeta-χ-caroten-2'-one as brown crystals. The yield corresponds to 92.1% of theory, although the product requires a further purification.

For the purpose of purification, 22.0 g of the product are dissolved in 220 ml of methylene chloride. 220 ml of methanol are added dropwise to the solution while stirring within an hour and a half. This brings about crystallization, and the resulting suspension is stirred at room temperature for 30 minutes. The crystals are then filtered off over a sintered glass suction filter and washed twice with 50 ml of methanol each time. Finally, the crystals obtained are dried for about 16 hours at 50° C. under reduced pressure (vacuum drying oven).

In this manner there are obtained 17.04 g (67.1% of theory) of 1'-hydroxy-16'-(3-methylbut-2-enyl)-1',2'-dihydrobeta-χ-caroten-2'-one as very dark grey crystals.

$^1$H-NMR (CDCl$_3$, TMS as internal standard): δ=1.03 ppm (s,6H), 1.38 ppm (s,3H), 1.45–1.48 ppm (m,2H), 1.54 ppm (s,3H), 1.58–1.65 ppm (m,5H), 1.72 ppm (s,3H), 1.73–1.83 ppm (m,3H), 2.00–2.08 ppm (m,17H), 4.16 ppm (s,1H), 5.03–5.05 ppm (m,1H), 6.11–6.77 ppm (m,17H), 7.54+7.58 ppm (d,1H).

We claim:

1. A process for the manufacture of a polyene (di)alcohol of the general formula

or, respectively,

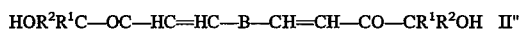

wherein

R$^1$ is a C$_{1-6}$-alkyl group and

R$^2$ is a C$_{1-6}$-alkyl group or a C$_{2-6}$-alkenyl group or

R$^1$ and R$^2$ together form 1,4-tetramethylene or 1,5-pentamethylene, and

A is a monovalent optionally substituted conjugated polyene chain connected at the terminal position of this chain, and B is a divalent optionally substituted conjugated polyene chain connected at the terminal positions of this chain, which process comprises reacting an optionally substituted conjugated polyene aldehyde of the general formula

or

wherein A and B are as above, the formyl group or, respectively, the two formyl groups being situated at the terminal position(s) of the conjugated polyene chain A or B, with cyclocarbonate or a derivative thereof of the general formula

wherein

R$^1$ and R$^2$ have the significances given above, under basic conditions to form said polyene (di)alcohol.

2. A process according to claim 1, wherein the polyene aldyhyde is a compound of the general formula

wherein
R is a group (a), (b) or (c)

8. Compounds of the general formula $$R''-CH=CH-CO-C(CH_3)_2OH \qquad II'''$$

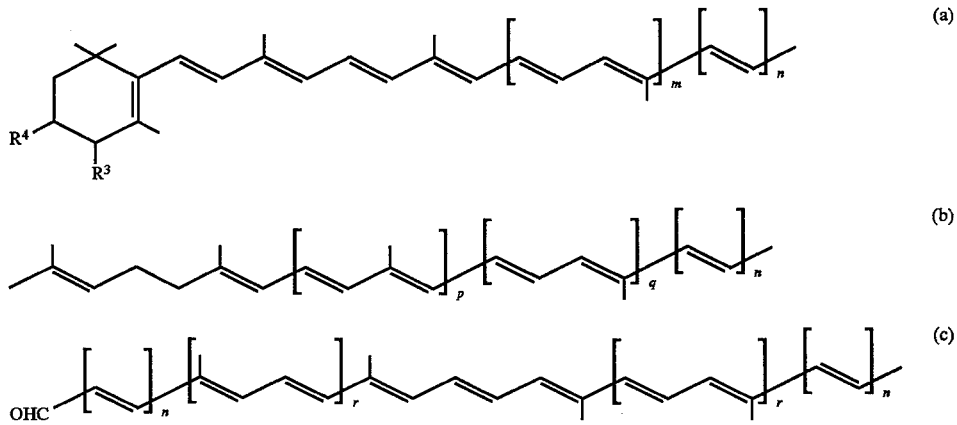

in which $R^3$ and $R^4$ each independently is hydrogen, an optionally protected hydroxy group or an optionally protected oxo group, m is 0, 1, 2, 3 or 4, n is 0 or 1, p is 0, 1 or 2, wherein R" is a group (a'), (b') or (c')

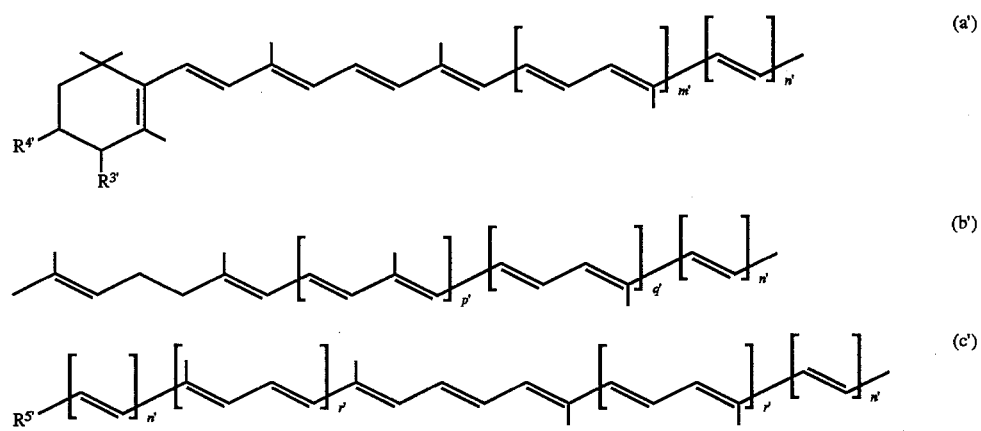

q is 0, 1, 2 or 3 and r is 0, 1 or 2, with one of the two formyl groups being optionally protected in the case of the compound of formula I in which R is group (c).

3. A process according to claim 1, wherein the polyene aldehyde is reacted with 1 to 5 equivalents of the cyclocarbonate or derivative thereof in an organic or aqueous-organic solvent in the presence of a base at temperatures from about 25° C. to about 120° C.

4. A process according to claim 3, wherein the organic solvent is a lower alcohol, a cyclic ether, an aromatic or a halogenated lower aliphatic hydrocarbon.

5. A process according to claim 3, wherein an alkali hydroxide or an alkali alkoxide is used as the base.

6. A process according to claim 3 wherein the reaction is carried out at temperatures from about 40° C. to about 80° C.

7. The process of claim 1, wherein the cyclocarbonate is 4,4-dimethyl-5-methylene-1,3-dioxolan-2-one.

and $R^{3'}$ and $R^{4'}$ each independently is hydrogen, an optionally protected hydroxy group or an optionally protected oxo group, m' is 0, 1, 2, 3 or 4, n' is 0 or 1, p' is 0, 1 or 2, q' is 0, 1, 2 or 3, r' is 0, 1 or 2 and $R^{5'}$ is either the 4-hydroxy-4-methyl-3-oxo-1-pentenyl group, the formyl group or a protected formyl group, and with the provisos that (i) with respect to group (a') m' is other than 2 or 3 when simultaneously $R^{3'}$ is hydrogen or an optionally protected oxo group, $R^{4'}$ is hydrogen and n' is 0; and m' is other than 3 when simultaneously $R^{3'}$ is an optionally protected hydroxy group, $R^{4'}$ is hydrogen or an optionally protected oxo group and n' is 0;

(ii) with respect to group (b') q' is other than 3 when p' is 2 and n' is 0; and (iii) with respect to group (c') r' is other than 2 when n' is 0.

9. A compound of claim 8, selected from the group consisting of:

13'-Hydroxy-13',14'-dihydro-12'-apo-β-caroten-14'-one,

9'-hydroxy-9',10'-dihydro-8'-apo-β-caroten-10'-one, (all-E)-2-hydroxy-2,6,10,14,18,23,27-heptamethyl-29-(2,6,6-trimethyl-cyclohex-1-enyl)-nonacosa-4,6,8,10,12,14,16,18,20,22,24,26,28-tridecaen-3-one, 7'-hydroxy-7'-methyl-7',8'-dihydro-9'-nor-6'-apo-β-caroten-8'-one, 5,5'-dihydroxy-5,6,5',6'-tetrahydro-4,4'-diapo-ψ,ψ-carotene-6,6'-dione, 2-hydroxy-2,6,11,15-tetramethyl-17-(2,6,6-trimethyl-3-oxo-cyclohex-1-enyl)-heptadeca-4,6,8,10,12,14,16-heptaen-3-one, 2-hydroxy-17-(4R-hydroxy-2,6,6-trimethyl-cyclohex-1-enyl)-2,6,11,15-tetramethyl-heptadeca-4,6,8,10,12,14,16-heptaen-3-one, 2-hydroxy-25-(4R-hydroxy-2,6,6-trimethyl-cyclohex-1-enyl)-2,6,10,14,19,23-hexamethyl-pentacosa-4,6,8,10,12,14,16,18,20,22,24-undecaen-3-one and (4E,6E,8E,10E,12E,14E,16E,18E)-2-hydroxy-2,6,11,15,19,23-hexamethyl-tetracosa-4,6,8,10,12,14,16,18,22-nonaen-3-one.

10. Compounds of the general formula

R'''—CH=CH—CO—CR¹'R²'OH     II'''' wherein

R''' is a group (a), (b) or (c)

m is 0, 1, 2, 3 or 4, n is 0 or 1,

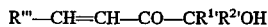 is 0, 1, 2 or 3 and r is 0, 1 or 2, with the formyl group either being free, protected or replaced by the —CH=CH—CO—R¹'R²'OH group when R''' is group (c), and R¹' is a $C_{1-6}$-alkyl group and R²' is a $C_{1-6}$-alkyl group or a $C_{2-6}$-alkenyl group or R¹' and R²' together form 1,4-tetramethylene or 1,5-pentamethylene, with the proviso that at least one of R¹' and R²' is other than methyl.

11. A compound of claim 10, selected from the group consisting of:

all-E-(R/S)-3-Hydroxy-3,7,11,15,20,24-hexamethyl-26-(2,6,6-trimethyl-cyclohex-1-enyl)-hexacosa-5,7,9,11,13,15,17,19,21,23,25-undecaen-4-one, 3-ethyl-3-hydroxy-7,11,15,20,24-pentamethyl-26-(2,6,6-trimethyl-cycohex-1-enyl)-hexacosa-5,7,9,11,13,15,17,19,21,23,25-undecaen-4-one and

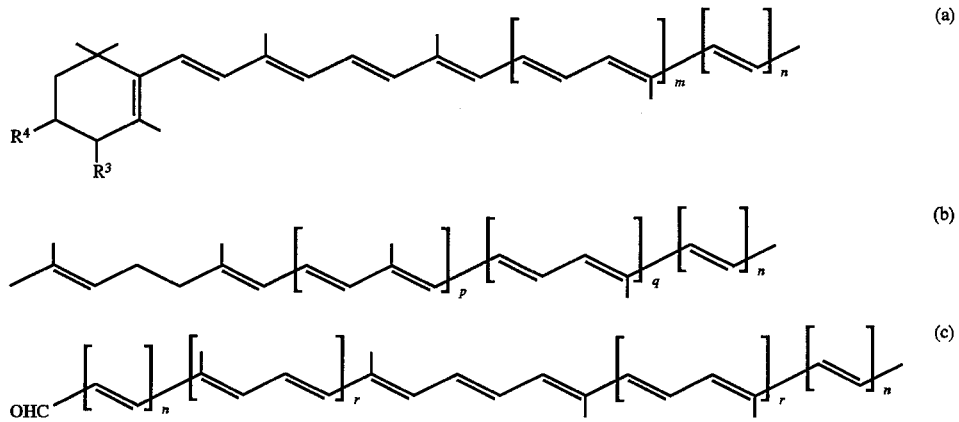

in which

R³ and R⁴ each independently is hydrogen, an optionally, protected hydroxy group or an optionally protected oxo group, 1'-hydroxy-16'-(3-methylbut-2-enyl)-1',2'-dihydrobeta-χ-caroten-2'-one.

* * * * *

UNITED STATES PATENT AND TRADEMARK OFFICE
CERTIFICATE OF CORRECTION

PATENT NO. : 5,648,550
DATED : July 15, 1997
INVENTOR(S) : Andreas Brüngger, Hansjörg Gründler & Werner Simon It is certified that error appears in the above-indentified patent and that said Letters Patent is hereby corrected as shown below:

Claim 10, line 14, before "is 0, 1, 2 or 3" insert -- p --.

Signed and Sealed this

Twenty-fifth Day of November, 1997

Attest:

BRUCE LEHMAN

*Attesting Officer*  *Commissioner of Patents and Trademarks*